(12) United States Patent
Hakki et al.

(10) Patent No.: US 9,289,593 B1
(45) Date of Patent: Mar. 22, 2016

(54) ENDOVASCULAR ELECTRODE SYSTEM FOR TISSUE STIMULATION

(71) Applicants: A-Hamid Hakki, Dunedin, FL (US); A-Hadi Hakki, Largo, FL (US)

(72) Inventors: A-Hamid Hakki, Dunedin, FL (US); A-Hadi Hakki, Largo, FL (US)

( * ) Notice: Subject to any disclaimer, the term of this patent is extended or adjusted under 35 U.S.C. 154(b) by 70 days.

(21) Appl. No.: 13/649,792

(22) Filed: Oct. 11, 2012

Related U.S. Application Data

(60) Provisional application No. 61/545,913, filed on Oct. 11, 2011.

(51) Int. Cl.
*A61N 1/18* (2006.01)
*A61N 1/05* (2006.01)

(52) U.S. Cl.
CPC ..................................... *A61N 1/05* (2013.01)

(58) Field of Classification Search
CPC .................................................. A61N 1/3756
USPC ............................................ 607/2, 115, 128
See application file for complete search history.

(56) References Cited

U.S. PATENT DOCUMENTS

| | | | |
|---|---|---|---|
| 5,224,491 A * | 7/1993 | Mehra | 607/126 |
| 5,282,845 A * | 2/1994 | Bush et al. | 607/128 |
| 5,383,922 A | 1/1995 | Zipes et al. | |
| 5,749,833 A | 5/1998 | Hakki et al. | |
| 5,902,331 A | 5/1999 | Bonner et al. | |
| 6,148,237 A | 11/2000 | Das | |
| 6,161,029 A * | 12/2000 | Spreigl et al. | 600/381 |
| 6,185,464 B1 | 2/2001 | Bonner et al. | |
| 6,219,581 B1 | 4/2001 | Schaldach et al. | |
| 6,256,543 B1 | 7/2001 | Spence | |
| 6,345,198 B1 | 2/2002 | Mouchawar et al. | |
| 6,370,427 B1 | 4/2002 | Alt et al. | |
| 6,400,992 B1 | 6/2002 | Borgersen et al. | |
| 6,434,430 B2 | 8/2002 | Borgersen et al. | |
| 6,445,953 B1 * | 9/2002 | Bulkes et al. | 607/33 |
| 6,505,081 B1 | 1/2003 | Das | |
| 6,529,777 B1 | 3/2003 | Hedberg et al. | |
| 6,544,270 B1 | 4/2003 | Zhang | |
| 6,574,512 B1 | 6/2003 | Zhang et al. | |
| 6,654,638 B1 | 11/2003 | Sweeney | |

(Continued)

FOREIGN PATENT DOCUMENTS

| | | | |
|---|---|---|---|
| WO | 9713941 A1 | 4/1997 | |
| WO | 9832485 A1 | 7/1998 | |

(Continued)

OTHER PUBLICATIONS

Lee KL, et al., First Human Demonstration of Cardiac Stimulation with Transcutaneous Ultrasound Energy Delivery: Implications for Wireless Pacing with Implantable Devices. J Am Coll Cardiol. 2007;50:877-83.

(Continued)

*Primary Examiner* — Alyssa M Alter
(74) *Attorney, Agent, or Firm* — Rosenberg, Klein & Lee

(57) ABSTRACT

An electrical lead system includes a shaft to which a series of expandable ring electrodes are attached that follows the contour of the vascular or muscular structures of the heart, such as cardiac veins, arteries, atrial appendages and trabeculae, and provides sensing of electrical cardiac impulses, pacing and high voltage shock or defibrillation. The lead system uses a variety of energy sources to stimulate the heart, such as ultrasound, electromagnetic and electric impulses.

18 Claims, 6 Drawing Sheets

(56) References Cited

U.S. PATENT DOCUMENTS

| | | |
|---|---|---|
| 6,654,644 B2 | 11/2003 | Sanchez-Zambrano |
| 6,658,289 B2 | 12/2003 | Helland |
| 6,671,562 B2 | 12/2003 | Osypka et al. |
| 6,675,045 B2 | 1/2004 | Mass et al. |
| 6,721,600 B2 | 4/2004 | Jorgenson et al. |
| 6,772,015 B2 | 8/2004 | Dahl et al. |
| 6,788,972 B2 | 9/2004 | Prutchi et al. |
| 6,795,732 B2 | 9/2004 | Stadler et al. |
| 6,856,835 B2 | 2/2005 | Bardy et al. |
| 6,868,291 B1 | 3/2005 | Bonner et al. |
| 6,871,101 B2 | 3/2005 | Zhang et al. |
| 6,885,889 B2 | 4/2005 | Chinchoy |
| 6,936,040 B2 | 8/2005 | Kramm et al. |
| 6,968,236 B2 | 11/2005 | Hagele |
| 6,973,351 B2 | 12/2005 | Morgan |
| 6,980,850 B1 | 12/2005 | Kroll et al. |
| 6,980,853 B2 | 12/2005 | Miyoshi et al. |
| 6,985,777 B2 | 1/2006 | Tsuboi et al. |
| 6,988,001 B2 | 1/2006 | Greatbatch et al. |
| 6,993,379 B1 | 1/2006 | Kroll et al. |
| 6,998,001 B2 | 2/2006 | Woelfel |
| 7,031,774 B1 | 4/2006 | Doan et al. |
| 7,047,086 B2 | 5/2006 | Taskiran et al. |
| 7,092,766 B1 | 8/2006 | Salys et al. |
| 2002/0035381 A1* | 3/2002 | Bardy et al. ............... 607/4 |
| 2002/0193836 A1 | 12/2002 | Schmidt |
| 2004/0176672 A1* | 9/2004 | Silver et al. ............ 600/345 |
| 2008/0255642 A1* | 10/2008 | Zarins et al. ............ 607/99 |

FOREIGN PATENT DOCUMENTS

| | | |
|---|---|---|
| WO | 0004950 A2 | 2/2000 |
| WO | 02087501 A2 | 11/2002 |
| WO | 2004045675 A2 | 6/2004 |
| WO | 2006083617 A2 | 8/2006 |

OTHER PUBLICATIONS

Mark Schoenfeld, Contemporary Pacemaker and Defibrillator Device Therapy: Challenges Confronting the General Cardiologist. J. Am. Heart Association. 2007; 115:638-53.

* cited by examiner

ENDOVASCULAR ELECTRODE SYSTEM FOR TISSUE STIMULATION

REFERENCE TO RELATED APPLICATIONS

This Patent Application is based on Provisional Patent Application Ser. No. 61/545,913 filed on 11 Oct. 2011.

FIELD OF THE INVENTION

The invention relates to the field of cardiology and in particular to systems for pacemaker implantation. More specifically, the present invention relates to a pacemaker lead system designed to provide pacing of the tissue by an intravascular self retaining electrode system, and a generator capable of detecting and inducing electrical and mechanical cardiac action. The system is capable of sensing myocardial electrical impulses, as well as providing low and high voltage pacing and defibrillation. It is another object of the present invention to allow pacing using electric, ultrasound or magnetic stimulation. The present invention additionally permits wireless stimulation of the tissue. It is another object of the current invention to provide simultaneous pacing of right and left cardiac chambers by way of intravascular electrodes to treat heart failure. It is yet another object of the present invention to cause a homogenous electric field for defibrillation.

BACKGROUND OF THE INVENTION

Conventional cardiac pacemakers and defibrillators consist of a generator for an electricity source and an elongated flexible pacemaker lead that is connected proximally to a header structure on the generator and is implanted distally within the heart for cardiac pacing and defibrillation. A lead is in actuality a bare segment of an insulated wire. The cardiac lead is configured with a tubular electrically insulated sleeve structure that is inserted into the body through an incision overlying veins leading to the heart chambers where the distal end of lead is lodged. The distal end of the lead is connected to a tubular tip electrode, having an increased diameter forming an annular shoulder against which the distal end of the sleeve abuts.

Biocompatible silicone based adhesives are used to connect the distal end of the lead sleeve and the tip electrode. Among the limitations of adhesives is that the manufacturing of the assembled lead requires sufficient time for the adhesive to cure, and the adhesive's bond strength may decrease in time and permit separation of the tip electrode from the sleeve.

One or more ring-type electrodes are secured to the sleeve proximal to the tip electrode: A flexible stylet is used to maneuver the lead to a desired position in cardiac chambers or veins with the guidance of real time imaging fluoroscopy. This is where cardiac stimulation occurs by contact with cardiac tissue.

Two conventional anchoring mechanisms are typically employed for fixing the distal end of a lead to cardiac tissue. An active fixation mechanism usually involves a screw-in electrode tip. A passive fixation mechanism consists of one or more radial tines that engage the inner lining of the heart or blood vessels.

Two conventional stimulation devices are typically employed, a single chamber device and dual chamber device. A single chamber system is capable of sensing and pacing in one chamber, either in the atrium or in the ventricle. Dual chamber stimulation devices are capable of sensing and pacing in both chambers, that is, in both the atrium and ventricle. Modes of pacing include VDD, DVI, VVI, and DDD, where the first letter indicates the chamber being paced, and the second letter indicates the chamber being sensed, while the third letter indicates inhibited or triggered responses. A fourth letter "R" denotes rate responsive pacing to match a patient's activities. In addition to pacing the right atrium and right ventricle, pacing the left ventricle via the cardiac veins, or biventricular pacing, provides more physiologic and synchronous cardiac contraction, and may improve cardiac function.

A lead system consists of one or more leads, conductor coils, and electrodes. The conductor coil is the internal core of the lead though which electric current flows. The lead is an insulated wire that connects the stimulator to the cardiac tissue. The lead carries impulses to the tissues one the one hand, and cardiac signals back to the sensing circuitry of the stimulator or generator on the other.

There are basically two types of leads, unipolar and bipolar. A unipolar lead has one conductor coil, with typically a cathode, or negative pole, at the distal tip and an anode, or positive pole, defined by the housing of the stimulator. The electric current returns to the anode via body tissue as a current path. A bipolar lead has two conductor coils, the distal tip forming a cathode, and an annular or ring electrode located a few millimeters proximal to the distal tip. For purposes of delivering high voltage defibrillation, one or two shocking coils are inserted intravenously.

Pacemaker leads are generally suited for placement in the ventricle and atrium. In order to provide permanent pacing and to avoid pacemaker lead dislodgment, various methods have been use to anchor the leads to the endocardium (the inner lining of the heart chambers). There has been increasing evidence in the literature that conventional right ventricular apical pacing alters the normal synchronization of different heart chambers, and may adversely influence ventricular function, leading to heart failure (inability of the heart to pump the required volume of blood) and increased mortality. Mark H. Schoenfeld reviewed the literature and pointed out the potential adverse consequences of right ventricular apical pacing (Circulation 2007; 115:638-653).

Alternative pacing sites from the His bundle, right ventricular outflow pacing, coronary sinus and cardiac veins have been utilized. Biventricular pacing or resynchronization requires the placement of electrodes inside the venous system of the heart. However, other than lodging the tip of the lead into the distal coronary vein, there is no safe anchoring mechanism to keep the lead from dislodging. Moreover, the best lodging site may not be the ideal pacing location for effective myocardial stimulation. Thus screw-in anchor may apply to the myocardium, but cannot be utilized in vascular structures due to the risk of endothelial damage and hemorrhage.

Another disadvantage of conventional pacemaker right ventricular leads is that they must cross the tricuspid valve. For that reason, the leads may cause unwanted tricuspid regurgitation by interfering with tricuspid valve closing during heart contraction. This may interfere with right ventricular function.

PRIOR ART

Conventional pacemaker generators permit sensing of electrical cardiac action by use of electrodes imbedded in the endocardium or vascular structures of the heart. Without electrodes, generators are unable to detect electrical or mechanical cardiac action. For a wireless system, it would be desirable for generators to detect and induce electrical and mechanical action. In addition, conventional generators are disc shaped and may not be suitable for operation in close proximity to cardiac structures. A curved and elongated shape generator would be desirable to conform to the intercostals space (the space between the ribs of the chest overlying the heart), and provide proximity to cardiac structures for transfer of electrical, ultrasound, Doppler, infrared and magnetic signals.

Kurth and Worley (U.S. Provisional Patent WO 2004/045675 A2) disclosed an introducer through which a pacemaker lead is guided. This introducer is formed with a distal end comprising an anchor attached to the walls of the cardiac chambers. Such fixed-in-place introducer allows steering of the pacemaker lead and prevents it from displacement or folding onto itself due to lack of support.

Robert J. Sweeney (U.S. Pat. No. 6,654,638) disclosed an ultrasonically activated implantable cardiac electrode system, whereby piezoelectric elements convert mechanical energy into electrical energy sufficient to cause pacing of cardiac tissue. The mechanical energy may originate from an external source low frequency ultrasound transmitter. The electrical energy produced by the piezoelectric element delivers pacing level electric energy between the system's anode and cathode. Sweeney describes active fixation elements using tines, hooks and barbs, but does not teach the use of an elongated generator that conforms to the curved spaces between the ribs for optimal acoustic window, or a wireless generator that functions to continuously measure cardiac electrical and ultrasonic and Doppler data. Nor does Sweeney's system use the data to send signals to the wireless ring electrodes. Thus, the ring electrodes do not require a power source, since the generator functions as the sensing apparatus and provides the logic necessary to synchronize the stimulation of tissues. A prior art algorithm is used to determine the timing and sequence of stimulation of cardiac tissues for generators attached to electrode wires imbedded in the cardiac chambers. Moreover, the pacing catheter Sweeney describes is not shaped to be self retaining, necessitating active fixation elements such as tines, hooks and barbs.

Lee et al. have demonstrated the feasibility of cardiac stimulation in humans using trans-cutaneous ultrasound (J Am Coll Cardiol 2007; 50:877-83). They inserted a receiver electrode at the tip of a 6-F steerable electrophysiologic catheter (EB Systems, Inc.). The receiver transducer contained circuitry that converted ultrasound energy to electric energy which was transmitted to a pair of bipolar electrodes. The cathode electrode comprised a 4 mm hemispherical platinum/iridium tip electrode, and a proximally located 2 mm anode. The ultrasound generator transmitted ultrasound with variable frequency, amplitude, pulse width, and cycle length. Electric output voltage on the electrodes was monitored during ultrasound pacing (Tektronix TDS 3014B, Beaverton, Oreg.). Lee et al. were able to consistently pace and capture in 77 out of 80 cardiac sites.

Paul A. Spence (U.S. Pat. No. 6,256,543) disclosed a temporary pacemaker lead having two connectors with releasable engagement, so as to permanently affix the electrode to the heart tissue. The electrode may be a tiny piece of metal such as a clip. When the lead wire is removed from the heart, it is released from the electrode, and may be re-attached if necessary.

In order to improve visibility on fluoroscopy, and bond strength of sleeve to electrode joints, Stephen D. Das (U.S. Pat. No. 6,256,543) disclosed a cardiac stimulator lead with annular members around the proximal and distal ends, and a flexible tubular sleeve made of biocompatible electrically insulating material such as silicone or polyurethane. He described (U.S. Pat. No. 6,505,081) a swaged distal electrode with a deformed annular member to eliminate the need for adhesive to metal bonding at the distal end of the sleeve and the tip electrode.

WO 2002/087501 (Quetzal Biomedical, Inc.) provided a multi-electrode lead with up to 258 electrodes placed on a nonconductive polymer tube. The V-shaped lead disclosed is used to stimulate the septum of the right ventricle.

WO 1998/032485 (Cardiac Pacemakers, Inc.) described an intravenous pacemaker lead with detachable positioning member having one or more electrodes implanted within the coronary veins, and techniques for advancing the leads through the atrium.

WO/2006/083617 proposed a cardiac harness configured to fit around the heart and comprising electrodes attached to a power source for pacing or defibrillation. Richard J. Hagele (U.S. Pat. No. 6,968,236) used magnetic resonance imaging (MRI) compatible cardiac electrodes made of ceramic, with ultra-thin conductive layer of platinum or titanium and housing sensing and pulse-delivering components.

Wilson Greatbach and Michael L. (U.S. Pat. No. 6,988,001) disclosed a hermetic component housing for photonic catheter connected to a photonic pacemaker designed to be compatible with magnetic resonance imaging (MRI).

Eckhard Alt, Richard Sanders, and Lawrence J. Stotts (WO 00/04950) provided a device and method for simultaneously pacing both right and left ventricles, in order to achieve homogeneous electric field suited for delivering defibrillation shock to the heart. The right heart chamber enables pacing modes such as VVI, VVI-R, DDD, DDD-R, AAI, AAI-R, as well defibrillation shocks when needed. Separate left ventricular lead and coil allow defibrillation thresholds as low as 2 to 3 joules. Such low energy requirement may be delivered by considerably smaller generators weighing less than 50 grams and having volumes of less than 30 milliliters. The leads include coil electrodes which are on separate electrical wires, but encompassed in the same sheaths, in the right atrium, right ventricle, and left ventricle.

John A. Schmidt (U.S. Application 10/135,061 published as US 2002/0193836) disclosed a multi-electrode array that is shaped to fit the right ventricle in order to distribute electrodes at different desirable locations to assist in the treatment of heart failure. The lead contains a separate hollow tube inside the polymer tubing for a stylet (a stiff wire to assist in lead implantation).

U.S. Pat. No. 6,885,889 addressed a method for optimizing cardiac re-synchronization therapy using an implantable or external stimulation device. Zipes et al (U.S. Pat. No. 5,383,922) disclosed a method for affixing implantable catheters and radiofrequency leads. The RF signal enables stabilization of the electrode by adherence to body tissues.

John R. Helland (U.S. Pat. No. 6,658,289) provided an implantable universal pacing and defibrillation device in all 4 chambers of the heart, using different electrode configurations for both atrial and ventricular defibrillation.

Stadler et al (U.S. Pat. No. 6,795,732) utilized implantable sono-micrometer output signals to measure mechanical heart performance, by measuring cardiac dimensions.

Alt et al (U.S. Pat. No. 6,370,427) allowed for simultaneous pacing of both ventricles to reduce the QRS width. The left ventricular lead is of a smaller diameter and is passed retrograde through the aortic valve.

Gust H. Bardy at al (U.S. Pat. No. 6,856,835) used biphasic waveforms for anti-tachycardia pacing, utilizing an implantable subcutaneous cardioverter-defibrillator implanted between the third rib and the twelfth rib without contact with the heart or blood vessels.

Borgersen et al (U.S. Pat. Nos. 6,434,430 and 6,400,992) disclosed a co-extruded multi-lumen cardiac lead for sensing, pacing, and defibrillation, using biocompatible electrically insulating materials of different durometers in different axial sections.

Dahl et al (U.S. Pat. No. 6,772,015) described a bifurcated lead system designed for different cardiac veins. The first elongated member or "thumb" portion is positioned within the coronary sinus or great cardiac vein, and the second or "finger" portion of the bifurcated distal tip is positioned within a branch tributary of the coronary sinus such as the posterior or middle cardiac vein.

Fuminori Tsuboi and Tetsuo Tanaka (U.S. Pat. No. 6,985,777) provided a lubricating coat layer for implantable electrodes and the ligation thereof.

Scott Salys, Peter Fong, and Phong D. Doan (U.S. Pat. No. 7,092,766) demonstrated an active fixation screw-in type of lead including a radio-opaque helical fixation element that is extendable and retractable.

Phong D. Doan and John R. Helland (U.S. Pat. No. 7,031,774) utilized a switch for implantable electrode selection in single-pass leads (atrium and ventricle). They used only one connector that could work with two or more sets of electrode pairs.

Conventional telemetry systems for implantable pacemakers utilize radio-frequency energy that allows bi-directional communication between the generator and external programmers, but require close proximity to each other. William R. Mass and Jeffrey A. Von Arx (U.S. Pat. No. 6,675,045) enabled far field radiofrequency communications with implantable medical devices using a split-can dipole antenna.

Matthew D. Bonner and Timothy G. Laske (U.S. Pat. Nos. 6,185,464, 6,868,291 and 5,902,331) addressed arrangements for implanting endocardial cardiac leads. They introduced an endocardial lead without a lumen for a stylet but placed over a guidewire already advanced to the desired site, and used a pusher to facilitate insertion. They described an elongated pusher body of flexible material extending between the pusher body proximal and distal ends, with cardiac lead engaging means to engage the distal lead end.

Murat Taskiran et al. (U.S. Pat. No. 7,047,086) used a single electrode probe with a bifurcating section for DDD pacing, and a configuration to be fixed in the atrium of the heart.

Kevin L. Morgan (U.S. Pat. No. 6,973,351) described an elongated multi-lumen tube and used composite materials for conductors and stylet insertion.

David Prutchi et al (U.S. Pat. No. 6,788,972) provided for measuring of pacing impedance of an electrode-tissue interface.

Thomas P. Osypka and Ronald van den Nieuwenhof (U.S. Pat. No. 6,671,562) utilized a drug eluting high impedance bipolar cardiac lead. The drug-eluting insulating member is disposed within the annular gap between the outer surface of the tip electrode and the inner surface of the ring electrode. They used multiple flexible tines at the distal portion of the lead for passive fixation.

Stephen D. Das (U.S. Pat. No. 6,505,081) and U.S. Pat. No. 6,142,237 used pacemaker leads with swaged distal electrodes.

Sergio Sanchez-Zambrano (U.S. Pat. No. 6,654,644) disclosed an extractable endocardial tip for an electrode of an electrical stimulator. A fin is provided with an anterior leading edge and a posterior receding serrated sharp cutting edge for cutting through fibrous tissue to facilitate withdrawal of the lead, and subsequent insertion.

In order to increase the lifespan of pacemaker batteries, less energy may be used by the pacemaker, such as with demand pacing where the pulse is delivered only when needed, and with pulse width or amplitude just minimized to just above the threshold value. Holmstrom et al (U.S. Pat. No. 6,529,777) provided a biocompatible piezoelectric tip or ring electrode adapted to be in direct contact with cardiac tissue for electrical and mechanical stimulation, and for detecting electrical and mechanical evoked responses.

Yongxing Zhang (U.S. Pat. No. 6,544,270) included a system with reduced diameter leads having a complete stylet, a partial stylet, or no stylet at all. The elongated catheter body has at least two lumens through which first and second leads pass.

Zhang et al (U.S. Pat. No. 6,574,512) disclosed a single pass endocardial lead comprising a main lead and a transverse lead. The transverse lead body extends laterally from the main lead body, and curves around and encircles the main lead.

Zhang et al (U.S. Pat. No. 6,871,101) describe a sleeve for passing the lead.

Mouchawar et al (U.S. Pat. No. 6,345,198) used single pass lead system in a bipolar fashion using a 3 electrode structure, the first electrode is arranged in the atrium, the second is arranged in the ventricle just below the tricuspid valve, and the third is arranged at the apex of the ventricle.

Schaldach et al (U.S. Pat. No. 6,219,581) disclosed a pacing lead system and electrode arrangements. The first pacing electrode is arranged in the superior vena cava, and the second pacing electrode is arranged either in the atrium or a blood vessel near the heart.

Kroll et al (U.S. Pat. Nos. 6,980,850 and 6,993,379) emulated a surface multiple lead EKG using signal detected by internal leads and employing a matrix based technique.

Kramm et al (U.S. Pat. No. 6,936,040) disclosed methods for positioning electrical pacing leads in cardiac veins by inserting a lead within the coronary sinus, and using agents to dilate cardiac veins.

Jorgenson et al (U.S. Pat. No. 6,721,600) provided implantable lead functional status monitoring of lead impedance and patient alert system for patients to seek help in the event of serious lead malfunction.

WO 1997/013941 described four chambers pacing for dilated cardiomopathy.

The present invention discloses a system that circumvents the limitations of the prior art, such as those mentioned above.

SUMMARY OF THE INVENTION

An implantable device and method are provided which serve to sense, pace, and shock various cardiac tissues. The device and method employ electrodes suitable for vascular structures, such as venous or arterial system, utilizing leads of different configuration. The leads are preferably collapsible in a pre-deployment configuration, and expanded for deployment once situated at the desire location.

DETAILED DESCRIPTION OF THE PREFERRED EMBODIMENTS

Figure 1:
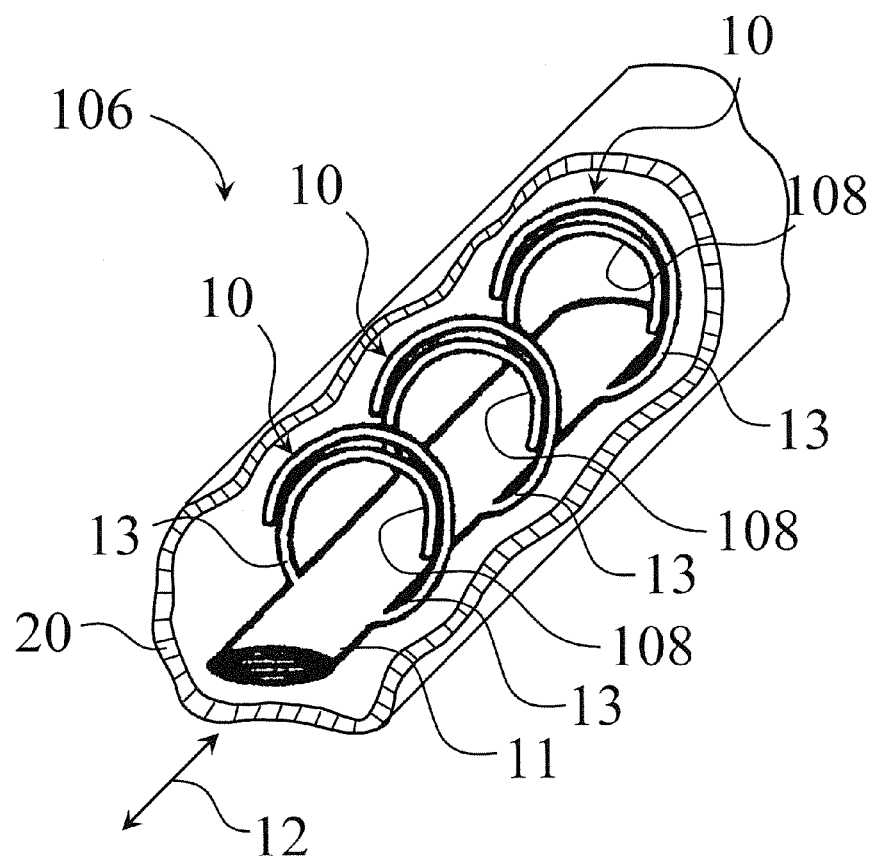
FIG. 1 is perspective view illustrating a system formed in accordance with an exemplary embodiment of the present invention, in a pre-deployment configuration.

The following description with reference made to the accompanying figures is not to be interpreted in a limited sense. It is to be noted that other embodiments may be utilized without departing from the scope of the current invention, as defined in the Claims appended to this description.

In accordance with the present invention, a pacemaker lead system generally comprises a series of expandable and collapsible ring electrodes. Each ring electrode includes two or more curved electrode portions that may overlap before deployment, and fan out when deployed, in order to conform to the shape of the vascular or cardiac structure at which it is deployed. This facilitates endothelialization of the electrodes by the body fluids and cells.

Referring now to FIGS. 1-6, there is shown a system (8) for generating and sensing electrical energy to and from mammalian tissue within a patient body and/or the wall of a mammalian vessel or patient's vessel (20) and may include generator (51) adapted to be received within body (100) of the patient and particularly, in the intercostals region (102) located between patient ribs (104). Alternatively, electrical generator (65) may be located external the patient's body (100) for wireless transmission of electrical energy as will be discussed in following paragraphs. Thus, either electrical generator (51) or (65) produce and sense electrical energy passing to and from the wall of a mammalian vessel (20) within a patient's body.

Of importance is that the system (8) includes lead system (106) which includes the lead or shaft (11) which is coupled to either the generator (51) or (65) and is insertable within the vessel (20) or in proximity to mammalian tissue within a patient's body. The lead or shaft (11) includes a lead axis line (12) which may be curvilinear in extent due to the fact that lead or shaft (11) may be inserted into the patient's body in a tortuous contour. Lead system (106) further includes a plurality of expandable electrodes (10) coupled to the lead or shaft (11) on opposing sides thereof. Electrodes (10) are radially displaceable with respect to axis line (12) for providing contiguous contact with the patient's tissue or an inner wall of the vessel (20) when lead system (106) is in the deployed mode of operation.

Figure 2:
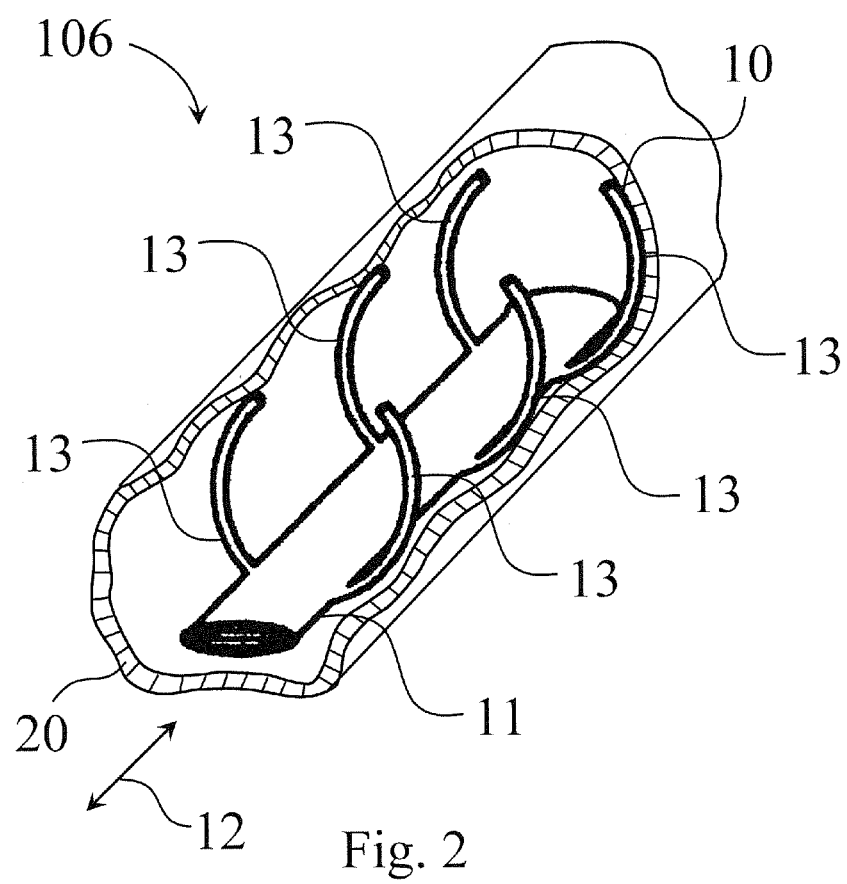
FIG. 2 is perspective view illustrating the embodiment of FIG. 1, in a deployment configuration.

FIG. 1 depicts lead system (106) in the pre-deployment stage where electrodes (10) are shown in overlapping relation to minimize the cross-sectional area for insertion into the vessel (20). FIG. 2 shows the pacemaker lead system (106) in a deployed position subsequent to expandable electrodes (10) being radially expanded. As FIG. 2 illustrates, in its deployed position, the radially expanded electrodes (10) contiguously contact an inner wall of vessel (20).

Each of electrodes (10) has a pair of arm members (13) extending from opposing sides of the shaft (11) as is seen in both FIGS. 1 & 2. Electrode arm members (13) may be formed of an electrically conductive metal composition for transmission of electrical energy. Electrode arms (13) may be formed of any type of electrically conductive composition with the only exception being that such be expandable in the radial direction and provide sufficient structural integrity to support the forces applied thereto during expansion and during operation within the patient's body and further being biocompatible with respect to the patient's body. Such electrically conductive compositions are well known in the art and will not be further discussed.

In general, lead system (106) may be formed of a plurality of expandable electrodes (10) each displaced from the other by a predetermined distance as is clearly seen in FIGS. 1 & 2.

Figure 4:
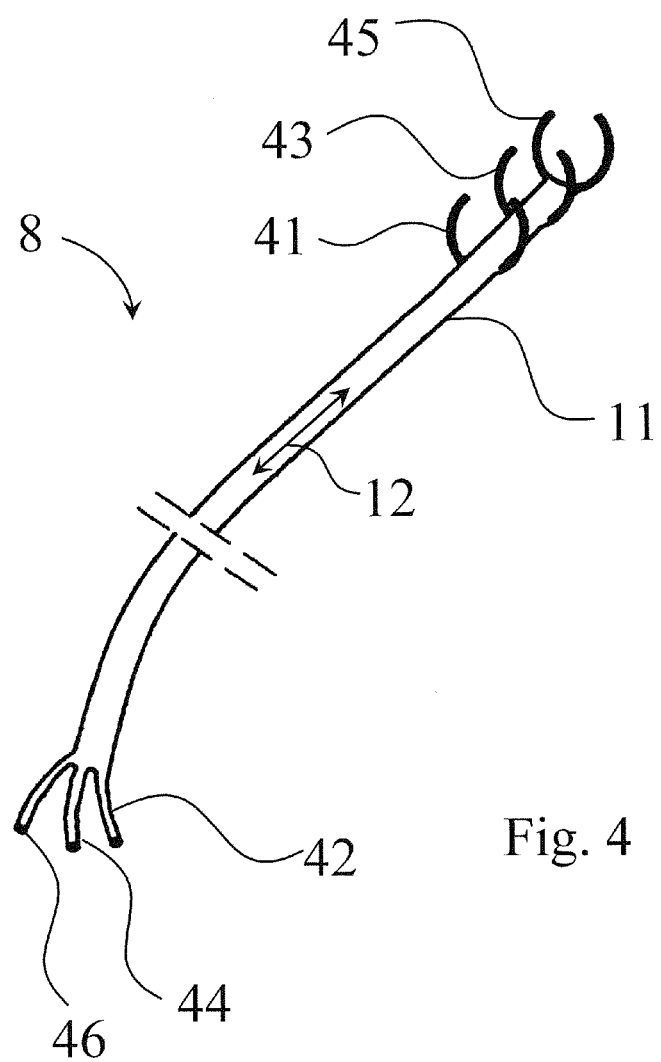
FIG. 4 is perspective view, partially cut away, illustrating an exemplary embodiment of the present invention incorporated into a catheter structure.

A system (106) adaptable for pacemaking is shown in FIG. 4 having high voltage pacing electrodes (45) coupled to high voltage pacing port (46). Low voltage pacing electrodes (43) are coupled to lead (11) and the electrical energy is passed through low voltage pacing port (44). System (106) may include sensing electrodes (41) which are electrically coupled to sensing port (42).

In certain exemplary applications, these ring-like electrodes (10) may be introduced percutaneously over a conventional balloon tipped catheter, or may be surgically implanted. Where a balloon tipped catheter is used, balloon inflation subsequent to introduction causes responsive expansion of the electrode rings so that they contact the lining of the cardiac chambers or vessel walls. The balloon (37) may then be deflated and the catheter extracted, leaving the electrodes (10) in contact with the vascular endothelium as shown in FIG. 2.

System (8) may include expansion mechanism (34) for radially displacing electrodes (10) into interfacing relationship with the inner wall of a patient's vessel (20). Expansion mechanism (34) may include a well-known balloon catheter which includes the balloon (37) for insert through the openings (108), shown in FIG. 1, and then expanded to deploy the expandable electrodes (10) into the deployed position as shown in FIG. 2. Balloon catheters are well-known in the prior art and have previously been used in particular for stent placement within a vessel. Once the balloon catheter has been inserted through the openings (108) through pressure differentials, expandable arm members (13) may be deployed.

Preferably, the ring electrodes (10) comprise ultrasound and electromagnetic receiver electrodes. Compared to prior art, the current invention provides such advantages as closer electrode contact with a larger surface area of tissue. With greater surface area of electrodes, less amount of energy is needed to stimulate tissue. Additionally, flat shaped electrodes may be provided (compared to the round cylindrical shaped conventional electrodes) for more effective endothelium coverage, minimizing the risk of clot formation.

In accordance with one embodiment of the present invention, wireless piezoelectric elements are thereby implanted within the vascular or muscular structures of the vascular system. Their stimulation by external or implantable ultrasound and Doppler transmitter measures allow for transduced wireless stimulation of the tissues, when the piezoelectric elements convert their externally stimulated mechanical energy to electrical energy. A self-retaining wireless implantable electrode system operable in this manner with piezoelectric elements is heretofore unseen.

In certain alternate embodiments, the ring electrodes are attached to a power source to enable sensing, low voltage pacing and high voltage pacing.

Conventional pacemaker generators permit sensing of electrical cardiac action by use of electrodes imbedded into the endocardium or vascular structures of the heart. Without electrodes, generators are unable to detect electrical or mechanical cardiac action. For a wireless system, it would be desirable that generators serve both to detect and induce electrical and mechanical action. In addition, conventional generators are disc shaped and may not be suitable for use in close proximity to cardiac structures. A generator having curved and elongated shape would be more desirable to conform to the intercostals space (the space between the ribs of the chest overlying the heart), and permit sufficient proximity to cardiac structures for effective transfer of electrical, ultrasound, Doppler, infrared and magnetic signals.

FIG. 1 shows an exemplary embodiment of a system formed in accordance with the present invention. The system includes a series of overlapping ring-shaped electrodes (10), as configured prior to deployment. For clearer illustration of its components, the system is shown separate from the balloon tipped catheter (illustrated in FIG. 3) which preferably carries the system's electrodes to their deployment position. The ring electrodes (10) are attached to a shaft (11) that has a low or flat profile, so as to minimally interfere with blood flow, and maintain contact with the lining of the surrounding tissues (such as blood vessels, or heart chambers). While electrodes (10) are shown having a circular cross-sectional shape in FIG. 1, such is provided for illustrative purposes only and may be configured to have alternative cross-sectional shapes, for example, a rectangular contour.

FIG. 2 illustrates the ring electrodes (10) in their deployed configuration. They may be placed in such configuration by inflating the balloon catheter (FIG. 3), whereby the ring electrodes are expanded to closely conform to the shape of the vessel or chamber that needs to be stimulated. Contact with the lining of the vessel or chamber is essential for body fluids to flow freely and tissue to grow to cover the electrodes with endothelium (lining of the vessels), such that clot formation may be prevented. The ring electrodes (10) and shaft (11) are made of a material that is flexible, and which conducts electricity. Piezoelectric components are incorporated with the electrodes (10), and/or with the shaft (11) of the electrodes.

Figure 3:
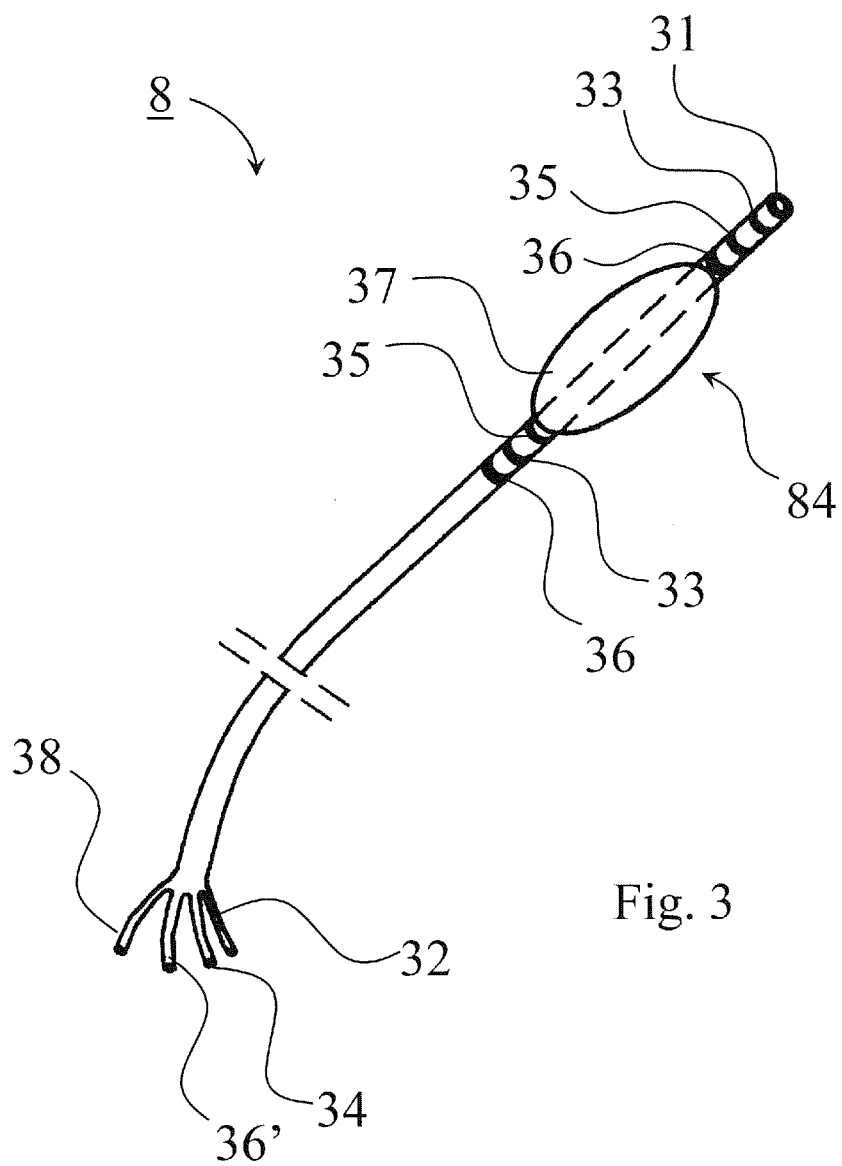
FIG. 3 is perspective view, partially cut away, illustrating a catheter usable to introduce the system of the present invention into a cardiac or intravascular structure of a patient.

FIG. 3 illustrates a balloon tipped multi-lumen catheter that may be used to carry the wireless ring electrodes to their destination. The catheter is equipped with flow meter, pressure manometer, and sensing and pacing electrodes to assist in proper positioning of the ring electrodes. The catheter is equipped with sensors to continuously monitors distal (31) and proximal (32) pressures, blood flow (33), and electrical thresholds (35), as well as with ultrasound imaging transducers (36). The balloon (37) is inflated and deflated from a proximal port (38).

Referring to FIG. 4, there is shown a representative multi-lumen catheter (40) provided with distal ring electrodes respectively for sensing (41), low voltage pacing (43), and high voltage pacing (45). The ring electrodes are coupled to corresponding proximal ports for, respectively, sensing (42), low voltage pacing (44) and high voltage pacing (46). Connections to an implantable generator are suitably made (not shown).

The catheter (40) is introduced over a temporary low profile balloon system (such as illustrated in FIG. 3) similar to that employed in prior catheters. Balloon inflation causes the distal ring electrodes to expand at the desired location in the given vascular system or heart chambers. Once the electrodes (10) are expanded to secure in place, the temporary balloon catheter is deflated and removed from the body, leaving the multi-lumen catheter in place.

Figure 5:
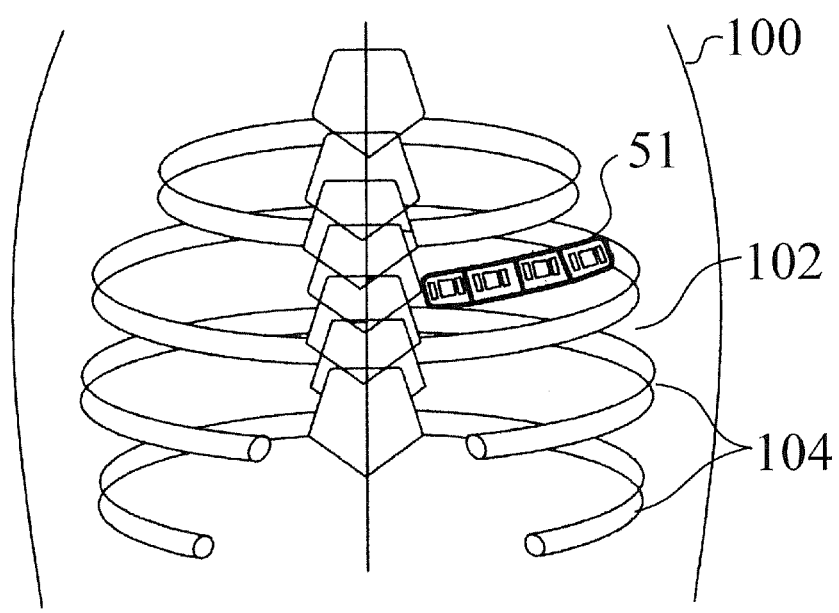
FIG. 5 is a perspective view, schematically illustrating a generator system disposed in an inter-costal space within the patient's anatomy; and, FIG. 6 is a perspective view of a generator system employed in accordance with an exemplary embodiment of the present invention.

FIG. 5 is a schematic diagram illustrating the inter-costal space (102), in close proximity with which expandable electrodes (10) of the present invention may have been deployed. An ideal location for a generator (51) would normally be free of intervening bone matter or lung tissue that might otherwise interfere with ultrasonic signals, which tend to transmit poorly through air present in lung tissue, and through bone matter.

Figure 6:
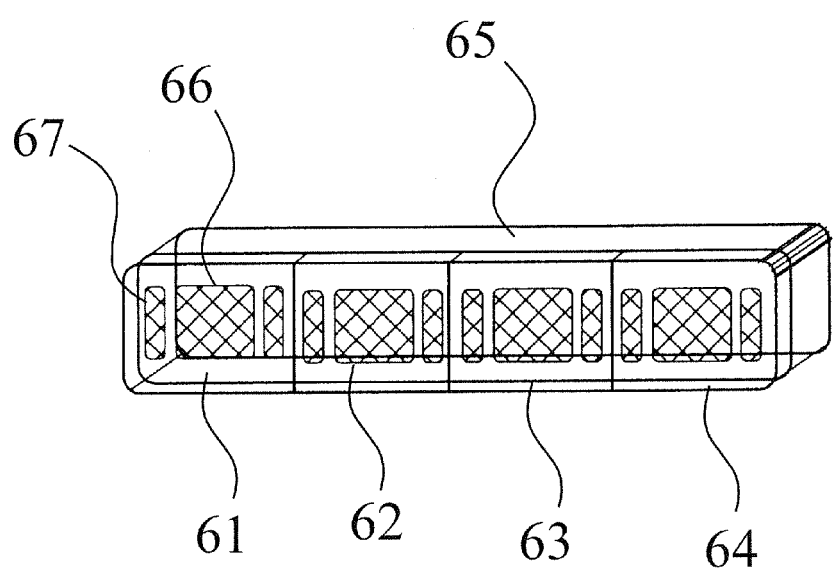

FIG. 6 shows a generator (65) such as disposed in the inter-costal space of FIG. 5. The generator (65) comprises elements for ultrasonic pacing (61), ultrasonic and Doppler imaging (62), low voltage pacing (63), and high voltage pacing (64). The generator (65) is surgically fixed within the inter-costal space at an optimum location determined by the ultrasonic (66) (or echocardiographic) window. Such imaging elements are disposed to face the heart or the tissue to be stimulated. The generator (65) also comprises electrocardiographic electrodes (67) which may face the heart or the ribs, or may even face away from the heart, depending on the level of inter-costal muscle interference with the heart's electrical signals. Preferably, the power source is positioned behind or beside the pacing or imaging elements, so as not to interfere with their function. The power source may be of any suitable type commercially available, such as electrochemical or electromechanical.

The generator (65) may be flexible, curved, or made of movable pacing and imaging elements so as conform to the spaces between the ribs, and minimize unwanted cosmetic chest asymmetry. We have previously shown the advantages of the close proximity of echocardiographic and electrocardiographic electrodes near the tip of trans-esophageal probes (Combined Echo-electrocardiographic Probe, A-Hamid Hakki et al, U.S. Pat. No. 5,749,833).

According to one aspect of the present invention, a convenient and effective method of securely implanting a pacemaker lead into the vascular system (veins, arteries or lymphatic channels) of the heart is provided.

According to certain embodiments of the present invention, a multi-lumen catheter is introduced into the venous system of the heart, implanting electrodes at various locations within the cardiac veins for optimal pacing. The locations are determined by the resultant pacing induced electrical and mechanical efficiency. Conventional steering mechanisms are utilized for introducing pacemaker leads and maneuvering in different cardiac chambers and vessels. Steerable flexible wire systems may be introduced via the multi-lumen catheter.

According to yet other embodiments of the present invention, a multi-lumen catheter is introduced into the venous system of the heart, implanting electrodes at various locations within the cardiac veins for optimal pacing. The ring electrodes are bipolar with distal cathode and proximal anode.

According to still other embodiments of the present invention, a multi-lumen catheter is introduced into the venous system of the heart, implanting electrodes at various locations within the cardiac veins for optimal pacing. The electrodes are detachable and embedded in the lining of the vessel.

In other embodiments, a multi-lumen catheter is introduced into the venous system of the heart, implanting electrodes at various locations within the cardiac veins for optimal pacing. The electrodes are made of suitable material such as platinum, iridium that provides optimal sensing, pacing, and shock.

In certain other embodiments, the ring electrodes are equipped with receiver transducer circuitry any suitable type known in the art capable of converting ultrasound energy to electric energy to be transmitted to the electrodes.

In certain other embodiments, a multi-lumen catheter is introduced into the arterial system of the heart, implanting electrodes at various locations within the cardiac arterial system for optimal pacing. The ring electrodes are made of suitable material known in the art to be resistant to thrombus formation.

In certain other embodiments, the electrodes are coated with suitable material known in the art to be resistant to thrombus formation.

In certain other embodiments, the electrodes are formed of a suitable material known in the art having drug eluting properties.

In certain other embodiments, the electrodes are located in vascular beds of each of the four cardiac chambers in order to provide homogeneous electrical stimulation and defibrillation.

In certain other embodiments, the generator that energizes the leads is powered by a battery, and produces electrical stimulation.

In certain other embodiments, the generator that energizes the leads is powered by a stimulator that produces electrical current via body tissue without the need for a wire lead.

In certain other embodiments, the generator produces ultrasound energy that is transmitted to the electrodes equipped with receiver transducer circuitry operable to convert ultrasound energy to electric energy for transmission to the electrodes.

In certain other embodiments, the generator is curved and elongated in shape in order to conform to the intercostal space (the space between the ribs of the chest overlying the heart), and permit close proximity to cardiac structures for optimal transfer of electrical, ultrasound, Doppler, infrared and magnetic signals therewith.

In certain other embodiments, the generator is operable to detect cardiac electrical activity without the use of intracardiac electrodes.

In certain other embodiments, the generator is operable to emulate a 12-lead electrocardiogram by detecting cardiac electrical activity from various locations of the heart.

In certain other embodiments, the generator is operable to induce cardiac electrical signals without the use of electrodes.

In certain other embodiments, the generator is operable to detect cardiac mechanical activity by way of ultrasound or Doppler signals without the use of intracardiac electrodes.

In certain other embodiments, the generator is operable to induce cardiac mechanical contraction by way of ultrasound signals without the use of wire electrodes.

In certain other embodiments, the generator is operable to receive cardiac electrical and mechanical action and synchronize the output signals to electrodes implanted in various cardiac chambers in order to provide optimal cardiac contraction and function.

What is claimed is:

1. A system for generating and sensing electrical energy to and from tissue within a mammalian body comprising:
   (a) an electrical generator configured to produce and sense electrical energy to and from said tissue;
   (b) a lead coupled to said generator configured to be insertable in proximity to said tissue, said lead having a lead axis line;
   (c) at least one expandable electrode coupled to said lead, said expandable electrode being radially displaceable with respect to said lead axis line defining a longitudinal direction for contiguous contact with a wall of said tissue, said expandable electrode including at least two arcuate arm members extending transverse said longitudinal direction from opposing lateral sides of said lead and having overlapping sections prior to said radial expansion of said at least one electrode, said arm members disposed in a singular plane each with respect to the other; and
   (d) a balloon catheter for insert within an opening formed by said at least one electrode having an arcuate contour forming said opening whereby said balloon catheter contacts an inner periphery of said at least one electrode and radially displaces said at least one electrode upon inflation of a balloon formed on said balloon catheter.

2. The system as recited in claim 1 where said lead is at least partially electrically conductive.

3. The system as recited in claim 1 including a plurality of expandable electrodes mounted to said lead, said plurality of electrodes each displaced from the other by a predetermined distance along said lead axis line.

4. The system as recited in claim 1 including a plurality of expandable electrodes mounted to said lead, said electrodes displaced each from the other along said lead axis line.

5. The system as recited in claim 4 where said plurality of electrodes are electrodes from the group consisting of high voltage pacing electrodes, low voltage pacing electrodes and parameter sensing electrodes.

6. The system as recited in claim 5 where said generator detects cardiac electrical activity from said parameter sensing electrode.

7. The system as recited in claim 5 where said generator detects cardiac mechanical activity from said parameter sensing electrode.

8. The system as recited in claim 1 where said generator is configured to be inserted into an intercostal space or adjacent a rib of a patient.

9. The system as recited in claim 1 where said generator is positionally located external a patient's body.

10. The system as recited in claim 1 where said generator is configured to be positionally located internal a patient's body.

11. The system as recited in claim 1 where said electrical generator is wirelessly coupled to said at least one expandable electrode.

12. The system as recited in claim 1 where said at least one expandable electrode includes at least a pair of arcuately contoured arm members, each of said pair of arcuately contoured arm members extending from opposing transverse sides of said lead.

13. The system as recited in claim 12 where each of said arcuately contoured arm members include a cross-sectional shape selected from the group of a rectangle contour, a circular contour, an oval contour and a polygonal contour.

14. The system as recited in claim 13 where said generator includes an ultrasound and Doppler source for pacing in proximity to said at least one electrode.

15. The system as recited in claim 14 where said generator includes an ultrasound and Doppler source for imaging a patient's heart along the spacing between a patient's ribs.

16. The system as recited in claim 1 including:
   (a) a plurality of arcuately contoured expandable electrodes where said electrodes extend from opposing transverse sides of said lead and form an axial through opening prior to a radial expansion of said expandable electrodes; and,
   (b) an expansion mechanism insertable within said axial through opening and configured to radially expand said plurality of arcuately contoured expandable electrodes into interfering relationship with an said tissue.

17. The system as recited in claim 16 where said expansion mechanism is a balloon catheter for insert into said axial opening and configured for expansion of said electrodes contiguous said tissue.

18. The system as recited in claim 17 where said generator is configured to conform to an intercostal space of a human patient and provide transfer of signals selected from the group of electrical signals, ultrasound signals, Doppler signals, infrared signals and magnetic signals.

\* \* \* \* \*